United States Patent [19]

Han

[11] Patent Number: 4,975,462

[45] Date of Patent: Dec. 4, 1990

[54] ANTIARTHRITIC α-ARYLCARBAMOYL CYANOACETIC ACID DERIVATIVES

[75] Inventor: William T. Han, Cheshire, Conn.

[73] Assignee: Bristol-Myers Company, New York, N.Y.

[21] Appl. No.: 226,102

[22] Filed: Jul. 29, 1988

[51] Int. Cl.$^5$ ............... C07C 255/13; C07C 255/17; 61K 31/275

[52] U.S. Cl. .................................. 514/513; 514/521; 558/392

[58] Field of Search ................. 558/392; 514/513, 521

[56] References Cited

U.S. PATENT DOCUMENTS

| | | | |
|---|---|---|---|
| 3,016,295 | 1/1962 | Davidson et al. | 514/521 |
| 3,406,183 | 10/1968 | Laliberte | 514/521 |
| 3,909,231 | 9/1975 | Lange | 514/521 |
| 4,061,767 | 12/1977 | Ertel et al. | 514/521 |
| 4,170,656 | 10/1979 | Hanifin, Jr. et al. | 514/521 |
| 4,173,650 | 11/1979 | Hanifin, Jr. et al. | 514/521 |
| 4,189,436 | 2/1980 | Hanifin et al. | 514/521 |
| 4,197,310 | 4/1980 | Hanifin, Jr. et al. | 514/521 |
| 4,254,047 | 3/1981 | Hanifin, Jr. et al. | 514/521 |
| 4,254,048 | 3/1981 | Hanifin, Jr. et al. | 514/521 |
| 4,254,049 | 3/1981 | Hanifin, Jr. et al. | 514/521 |
| 4,256,759 | 3/1981 | Walker | 514/521 |
| 4,435,407 | 3/1984 | Walker | 514/521 |
| 4,579,581 | 4/1986 | Kay et al. | 558/392 |
| 4,644,010 | 2/1987 | Walker | 514/521 |

FOREIGN PATENT DOCUMENTS

| | | | |
|---|---|---|---|
| 2555789 | 7/1977 | Fed. Rep. of Germany | 514/521 |
| 3217446 | 11/1983 | Fed. Rep. of Germany | 514/521 |
| 1112210 | 5/1968 | United Kingdom | 514/521 |

OTHER PUBLICATIONS

Conant, James Bryant, The Chemistry of Organic Compounds, The MacMillan Company, N.Y. p. 264 (1939).
J. Med. Chem., 1979, 22:1385–1389.
Arch. Pharm., 1929, 267:325–352 (Chem. Abst., 1929, 23:4193).

*Primary Examiner*—Mary C. Lee
*Assistant Examiner*—J. Richter
*Attorney, Agent, or Firm*—Mollie M. Yang; William T. Han

[57] ABSTRACT

Disclosed herein are novel α-arylcarbamoyl cyanoacetic esters, thioesters, and amides which exhibit anti-inflammatory/antiarthritic activities.

13 Claims, No Drawings

ANTIARTHRITIC α-ARYLCARBAMOYL CYANOACETIC ACID DERIVATIVES

BACKGROUND OF THE INVENTION

1. Field of the Invention

The present invention relates to α-arylcarbamoyl cyanoacetic acid derivatives active as anti-inflammatory and anti-arthritic agents, to their use in the treatment of inflammatory or arthritic conditions, and to pharmaceutical compositions containing the novel compounds. More particularly, the invention relates to the esters, thioesters, and amides of α-arylcarbamoyl cyanoacetic acid.

2. Description of Related Art

Benzoylacetonitrile (I) and its monofluoro analogues have been found to be effective inhibitors of adjuvant-induced arthritis in rats (J. Med. Chem., 1979, 22:1385–9). The same article, as well as U.S. Pat. No. 4,189,436, also discloses β-oxo-β-thiophenepropionitriles (II) as anti-arthritic agents.

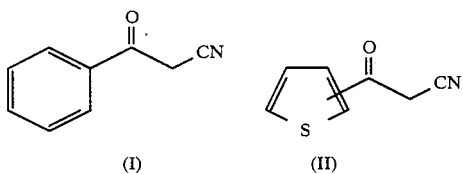

(I)  (II)

β-Oxopropionitriles having an α-carbonyl or thiocarbonyl substituent are reported as anti-inflammatory and/or anti-arthritic agents in (a) through (e):

(a) U.S. Pat. No. 4,061,767 and German Offenlegungsschrift No. 2,555,789 disclose, respectively, 2-hydroxyethylidenecyanoacetic acid anilide derivatives of formulas (IIIa) and (IIIb), wherein Ar is inter alia mono-, di-, or tri-substituted phenyl, said substituent may be, for example, halogen, alkyl, alkoxy, or halo-substituted alkyl.

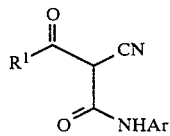

(III)

a: $R^1$ = methyl
b: $R^1$ = H, benzyl, $C_{2-17}$ alkyl (b) U.S. Pat. Nos. 4,254,047, 4,254,048, 4,254,049, 4,170,656, and 4,173,650 disclose a group of compounds that may be represented by the generic structure (IV) wherein X is oxygen, sulfur, methylene, or a direct bond; Ar is phenyl opt. substituted with one or more of the same or different groups selected from halogen, alkyl, alkoxy, trifluoromethyl, and trichloromethyl.

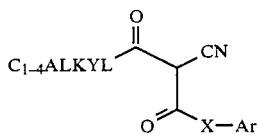

(IV)

(c) U.S. Pat. No. 4,197,310 discloses thiophenepropionitriles of formula (V) wherein R is hydrogen, lower alkyl, or halogen.

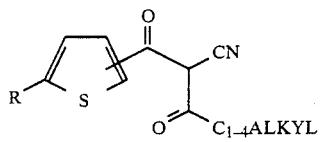

(V)

(d) U.S. Pat. Nos. 4,256,759, 4,644,010 and 4,435,407 disclose β-oxo-β-carbamoylpyrrolepropionitriles encompassed by generic formula (VI) where $R^1$ is H or alkyl; $R^2$ and $R^3$ are independently H or alkyl; and $R^4$ is phenyl or a heterocyclic radical both of which may be opt. substituted with alkyl, alkoxy, hydroxy, halogen, or trifluoromethyl.

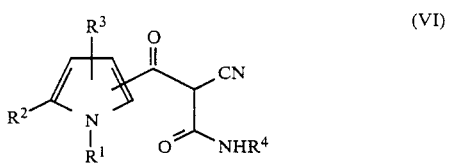

(VI)

(e) German Offenlegungsschrift No. 3,217,446 discloses thiocarbamoyl-thenoylacetonitriles of formula (VII) wherein $R^1$ is H, halogen, alkyl, or alkoxy; $R^2$ is $C_{3-6}$ cycloalkyl, benzyl, furfuryl, or phenyl opt. substituted with halogen alkyl, alkoxy, alkylthio, or trifluoromethyl.

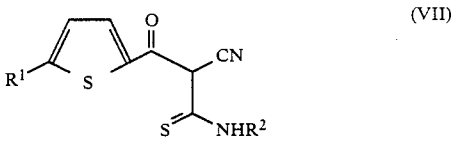

(VII)

Thus the 2-oxopropanenitrile antiarthritic agents disclosed in the prior art are all keto substituted compounds. Compounds of the present invention do not have a keto group; instead they have a carboxylic acid ester, thioester, or amide substituent. In this manner, compounds of the present invention are distinct over those disclosed in items (a) to (e) above.

A list of references disclosing cyanoacetic acid derivatives is given below; however, the compounds described therein have not been reported as anti-inflammatory or anti-arthritic agents.

(f) British Pat. No. 1,112,210 discloses 2-cyanomalonic acid thioamide derivatives of formula (VIII) wherein $R^1$ is inter alia alkyl or aralkyl; $R^2$ is H, alkyl, or aryl; and $R^3$ is alkyl or aralkyl.

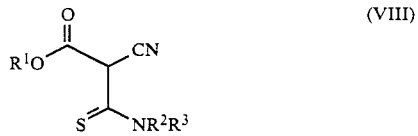

(VIII)

These compounds are said to be useful as bactericides, fungicides, and diuretics.

(g) U.S. Pat. No. 3,406,183 discloses 3-N-arylamino-3-mercapto-2-cyano-acrylamides of the formula (IX) wherein $R^1$ is H and $R^2$ is alkyl or phenyl; or $R^1$ and $R^2$ together represent $-(CH_2)_{4-5}-$; and Ar is opt. substituted phenyl.

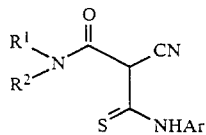

(IX)

These compounds are alleged to be useful as anthelmintic and antibacterial agents.

(h) Pabst (Arch. Pharm., 1929, 267:325-52) reported the preparation of a series of 2-cyanomalonamic acid esters and amides, for example, (X) and (XI).

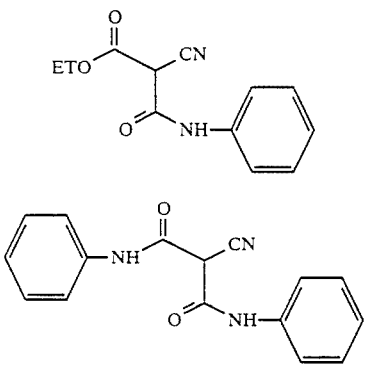

(i) U.S. Pat. No. 3,016,295 discloses 2-cyanomalonamic acid ester derivatives having formula (XII) wherein $R^1$ is alkyl or alkyl—$(OCH_2CH_2-)_{1-2}$ and $R^2$ is H or alkyl.

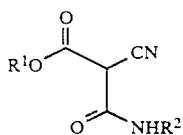

(XII)

These compounds are said to be useful in altering growth characteristics of plants.

U.S. Pat. No. 3,909,231 discloses the compound α-(3,4-dichlorophenyl)carbamoyl cyanoacetic acid ethyl ester as a bactericide and fungicide.

SUMMARY OF INVENTION

The present invention provides compounds having the formula (XIII)

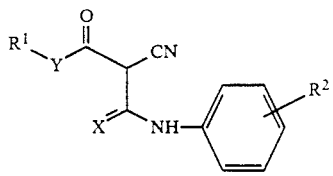

(XIII)

wherein $R^1$ is $C_{1-10}$ alkyl; X is O or S; Y is S, O, or NH; and $R^2$ is selected from the group consisting of H, halogen, $C_{1-5}$ alkyl, $C_{1-5}$ alkoxy, $C_{1-5}$ alkylthio, and halo-substituted $C_{1-5}$ alkyl; with the proviso that when Y is O or NH, $R^2$ is not H; or a pharmaceutically acceptable salt thereof.

A preferred embodiment provides compounds of formula (XIII) wherein X is O.

A further preferred embodiment provides compounds of formula (XIII) wherein $R^2$ is trifluoromethyl.

A further preferred embodiment provides compounds of formula (XIII) wherein Y is S.

A further aspect of the present invention provides a pharmaceutical composition which comprises an anti-inflammatory or an anti-arthritic effective amount of a compound of formula (XIII) and a pharmaceutically acceptable carrier.

Yet a further aspect of the present invention provides a method for treating a mammalian host afflicted with an inflammatory or arithritic condition which comprises administering to said host an anti-inflammatory or anti-arthritic effective amount of a compound of formula (XIII).

DETAILED DESCRIPTION OF THE INVENTION

As used herein, the term "alkyl" includes straight and branched carbon chain; "halogen" includes fluoro, chloro, bromo, and iodo; "halo-substituted alkyl" means alkyl substituted with one or more same or different halogen atoms.

Compounds of the present invention may exist in equilibrium with the enol form (XIIIa); however, for the sake of uniformity and convenience, the compounds are depicted as the keto form throughout the specification. It will be appreciated that the tautomeric hydrogen is sufficiently acidic to form salts with pharmaceutically acceptable inorganic or organic bases such as alkali metal or alkaline earth metal hydroxides; ammonia; mono-, di-, or trialkylamines; heterocyclic amines; or mono-, di-, or tri(hydroxyethyl) amines; these salts are also within the scope of this invention.

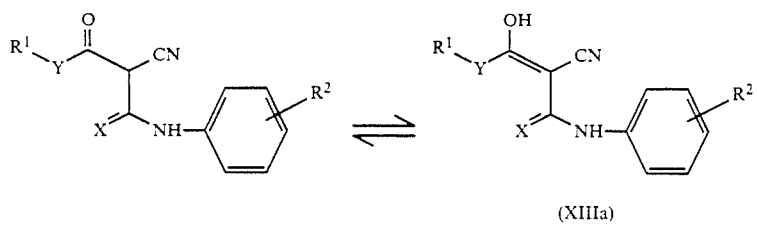

(XIIIa)

Compounds of the present invention may be prepared by methods known in the literature; in particular by reacting the anion of a cyanoacetic acid ester, thioester, or amide with an isocyanate or isothiocyanate.

Condensation of the cyanoacetic acid derivative with an isocyanate or an isothiocyanate may be effected in the presence of at least a molar equivalent, but preferably a slight molar excess, of an organic or an inorganic base. Suitable bases may be for example, an organic amine base such as triethylamine; an alkali metal hydride; an alkali metal hydroxide; or an alkali metal alkoxide. The reaction is carried out in an aprotic organic solvent such as toluene or tetrahydrofuran at or below ambient temperature for a period sufficient to substantially complete the reaction. The particular set of reaction conditions is dependent on the nature and reactivity of the reactants, and selection thereof is within the ability of one skilled in the art of chemical synthesis.

BIOLOGICAL ACTIVITY

Compounds of the present invention exhibit valuable pharmacological properties, in particular, anti-inflammatory and/or anti-arthritic activities. Representative compounds have been tested in the following in vivo models:

A. Modified developing adjuvant arthritis in rats.

This test is based on the procedure originally described by Pearson (Proc. Soc. Biol. Med., 1956, pp 91-5). Each experimental group used six male Lewis rats weighing approx. 250 gm. Arthritis was produced by a single intradermal injection of *Mycobacterium butyricum* (0.6 mg in 0.1 ml mineral oil) into the base of the tail. Test compounds were administered orally, once daily, starting on the day of inoculation (day 1) through day 8. The paw volume (average of two hind paws) was measured by the mercury displacement method at least twice weekly during the course of the experiment (40 to 42 days). The efficacy of a compound was expressed as the percent reduction of hind paw volume of treated vs. untreated rats using the following equation:

$$\% \text{ inhibition} = \frac{PC - RX}{PC - NC} \times 100$$

PC=positive control (not treated, arthritic)
NC=negative control (not treated, non-arthritic)
RX=drug group (treated, arthritic)

B. Carrageenin induced paw edema in the rat.

This test is based on the procedure originally described by Holsapple and Yim (Inflammation, 1984, 8:223). Six male Sprague Dawley rats weighing approx. 300 gm were used in each experimental group. The rats had been starved for 24 hours prior to injection of 0.1 ml of 1% carrageenin into the plantar surface of the left hind paw. Test compounds were dosed orally 30 minutes prior to carrageenin administration. The volumes of the left hind paws were measured by mercury displacement at 2,4, and 6 hours following carrageenin injection. The efficacy of a compound was expressed as the percent inhibition of carrageenin injected paw volume as compared to non-injected paw using the following equation:

$$\text{Percent Inhibition} = \frac{C - RX}{C} \times 100$$

C=Vehicle control group (left paw volume-right paw volume)
RX=Drug treated group (left paw volume-right paw volume)
The peak of drug effects usually occurred 2-4 hours following carrageenin injection.

Table I contains results of both the modified developing adjuvant arthritis and carrageenin induced paw edema models.

TABLE I

Activities in adjuvant-induced polyarthritis (AIP) and carrageenin-induced paw edema (CIP) models

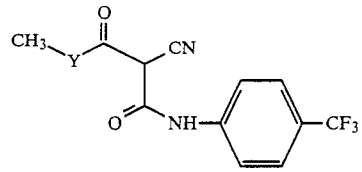

| Ex. # | Compound Y | Dose (mg/kg)[a] | AIP Inhib. score[b] d. 20-22 | AIP Inhib. score[b] d. 40-42 | CIP[c] |
|---|---|---|---|---|---|
| 1 | S | 50 | ++++ | ++++ | A |
| 2 | O | 100 | +++ | +++ | I |
| 3 | NH | 50 | +++ | +++ | A |

[a] once daily, p.o., from d. 1-8.
[b] % Inhibition of paw edema: O = <25; + = 25-<40; ++ = 40-<60; +++ = 60-80; ++++ = 80-100.
[c] test compound administered as a single oral dose of 50 mg/kg 30 min. prior to carrageenin injection. % Inhibition determined 4 hrs. after carrageenin injection; I = <25% reduction in paw volume and A = ≧25% reduction in paw volume.

Compounds of the present invention show good anti-inflammatory and/or anti-arthritic activities in the animal models used as demonstrated by the data in Table I.

Compounds of the present invention may be formulated into pharmaceutical dosage forms suitable for administration via convenient routes such as oral, intravenous, intramuscular, subcutaneous, topical and intraarticular. The formulated dosage forms may contain, in addition to the active agent, other pharmaceutically acceptable excipients to impart desirable pharmaceutical properties, for example, increased stability, improved taste, and improved appearance.

Compositions intended for oral administration may be in the form of tablets, pills, hard or soft gelatin capsules, powders, elixirs, syrups, and suspensions. Tablets, pills, powders and the like may contain additionally: a binder such as starch, gelatin, methylcellulose, or tragacanth; a disintegrant such as potato starch, alginic acid, or agar; a lubricant such as magnesium stearate, or polyethylene glycol; a diluent such as lactose, dextrose, mannitol, or cellulose; and/or other inert ingredients such as absorbants, colorants, flavoring agents, or sweeteners. Injectable compositions are preferably solutions or suspensions in a vehicle such as water, a pharmaceutically acceptable non-aqueous solvent, or a mixture thereof. They may contain, in addition to the active compound, preservatives (such as phenylmercuric nitrate, benzalkonium chloride, thimerosal, and benzyl alcohol), antioxidants (such as sodium bisulfite and acetone sodium bisulfite), emulsifiers, or buffers (such as citrates, acetates and phosphates). For intravenous administration, the unit dosage form may be diluted with conventional IV fluids such as sterile Water for Injection, NaCl Solution, or Ringer's Solution.

It will be appreciated that the actual preferred dosage of the compounds of the present invention will vary according to the particular compound being used, the particular formulation, mode of administration, and the severity of the disease being treated. Characteristics of the afflicted host such as sex, age, body weight, liver function, kidney function, and other concurrent drug therapies may also be considered by the attending clinician. Optimal dosages for a given set of conditions can be ascertained by those skilled in the art using conventional dosage determination tests in view of the experimental animal data provided.

The following examples are illustrative of the present invention and are not to be construed as limiting its scope.

EXAMPLE 1

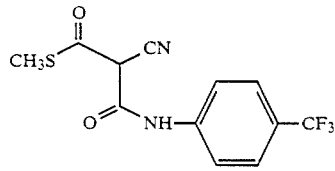

β-Methylthio-β-oxo-α-(4-trifluoromethylphenyl)carbamoylpropionitrile

A. S-Methyl cyanothioacetate

A cold solution of cyanoacetyl chloride (0.10 mole in 80 ml of benzene) was treated over 5 minutes with a solution of methanethiol (4.85 g, 0.10 mole) and TEA (11.13 g, 0.11 mole) in 25 ml of benzene. The resulting dark mixture was stirred at room temperature for 30 min., washed with 2×40 ml of water and dried over $Na_2SO_4$. Removal of the solvent gave a dark liquid that was chromatographed on 100 g of silica gel using methylene chloride-Skellysolve B (9:1). This yielded 6.65 g of S-methyl cyanothioacetate as yellow oil that was used without further purification.

B. β-Methylthio-β-oxo-α-(4-trifluoromethylphenyl)carbamoylpropionitrile

To a solution of the thioester (1.85 g, 16 mmoles) and TEA (1.62 g, 16 mmoles) in 30 ml of toluene at 10° C. was added 4-(trifluoromethyl)phenyl isocyanate (3.0 g, 16 mmoles) and the solution was stirred at ambient temperature for 2 h. The toluene was removed at reduced pressure and the syrupy residue, dissolved in 10 ml of $CH_3OH$, was poured into a cold stirred mixture of 75 ml water and 3 ml of 6N HCl. The precipitated solid was collected by filtration and recrystallized from acetone to yield the title compound (2.80g) as a white solid, mp 196°-198° C.

Anal Calcd for: $C_{12}H_9F_3N_2O_2S$: C, 47.68; H, 3.00; N, 9.27. Found: C, 47.41; H, 2.88; N, 9.25.

EXAMPLE 2

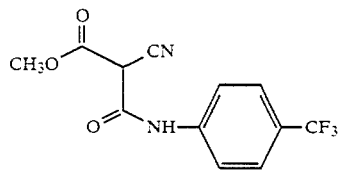

βMethoxy-β-oxo-α-(4-trifluoromethylphenyl)carbamoylpropionitrile

The anion of methyl cyanoacetate (2.20 g, 22.2 mmoles) was made at 0° C. using sodium hydride (0.8 g, 22 mmoles) in 70 ml of THF and treated dropwise with 4-trifluoromethylphenyl isocyanate (4.1 g, 22 mmoles). After one hour at 0° C. the solvent was removed and the residue was partitioned between 1N HCl and ethyl acetate. The organic layer was washed with brine, dried and partially concentrated in vacuo to precipitate the title compound (3.8 g) as a white solid, mp 186°-189° C.

Anal. Calcd for $C_{12}H_9F_3N_2O_3$: C, 50.35; H, 3.17; N, 9.79. Found: C, 50.42; H, 3.22; N, 9.83.

EXAMPLE 3

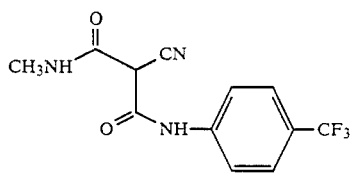

βMethylamino-β-oxo-α-(4-trifluoromethylphenyl)carbamoylpropionitrile

A. N-Methylcyanoacetamide

A mixture of cyanoacetic acid (10.0 g, 0.118 mole), oxalyl chloride (15.61 g, 0.123 mole) and 3 drops of DMF in 100 ml of dry benzene was stirred at ambient temperature until complete solution was obtained and gas evolution had ceased. The yellow acid chloride solution was chilled in an ice bath and excess methylamine gas was bubbled in to give a dark, gummy mixture that was stirred at room temperature for 1 h. Water was then added, the organic layer was separated and the aqueous solution was concentrated to near dryness. The slushy residue was slurried with warm ethyl acetate, filtered and the mother liquor was purified by flash chromatography on silica gel. Eluting the column with methylene chloride-ethyl acetate (85:15) gave the title compound (53% yield) which was used directly in the next step.

B. β-Methylamino-β-oxo-α-(4-trifluoromethylphenyl) carbamoylpropionitrile

Sodium hydride (0.82 g, 20.4 mmoles), washed with Skellysolve B, was suspended in 20 ml of dry THF and treated at 15° C. with N-methylcyanoacetamide (2.0 g, 20.4 mmoles) [prepared in Step A]. The resultant suspension was further cooled to 5° C. and 4-trifluoromethylphenyl isocyanate (3.80 g, 20.4 mmoles) was added over several minutes. After 18 h at ambient temperature the solvent was removed and the residual syrup was poured into a cold mixture of water and 4 ml of 6N HCl. The precipitate was isolated by filtration and recrystallized from ethanol to give 3.63 g of the title compound, mp 184°-186° C.

Anal. Calcd. for $C_{12}H_{10}F_3N_3O_2$: C, 50.53; H, 3.53; N, 14.73. Found: C, 50.46; H, 3.55; N, 14.63.

EXAMPLES 4-6

If the general procedures of Examples 1-3 are repeated using 4-(trifluoromethyl)phenyl isothiocyanate instead of 4-(trifluoromethyl)phenyl isocyanate, the corresponding thiocarbamoyl products are obtained.

EXAMPLE 7

The general procedure of Example 1, Step B is repeated with the following isocyanates or isothiocyanates instead of the 4-trifluoromethyl)phenyl isocyanate used therein to provide the corresponding carbamoyl products.

| Isocyanate | XIII (R¹ = CH₃; Y = S) | |
|---|---|---|
| | R2 | X |
| phenyl isocyanate | H | O |
| phenyl isothiocyanate | H | S |
| p-tolyl isocyanate | 4-CH₃ | O |
| o-tolyl isothiocyanate | 2-CH₃ | S |
| 3-chlorophenyl isothiocyanate | 3-Cl | S |
| 4-methoxyphenyl isocyanate | 4-OCH₃ | O |
| 2-ethylphenyl isocyanate | 2-CH₂CH₃ | O |
| 2-chlorophenyl isocyanate | 2-Cl | O |
| 3-chlorophenyl isocyanate | 3-Cl | O |
| 4-chlorophenyl isocyanate | 4-Cl | O |
| 2-chlorophenyl isothiocyanate | 2-Cl | S |
| 4-chlorophenyl isothiocyanate | 4-Cl | S |
| 2-methoxyphenyl isocyanate | 2-OCH₃ | O |
| 3-methoxyphenyl isocyanate | 3-OCH₃ | O |
| 2-methoxyphenyl isothiocyanate | 2-OCH₃ | S |
| 4-methoxyphenyl isothiocyanate | 4-OCH₃ | S |
| 2-bromophenyl isothiocyanate | 2-Br | S |
| 4-bromophenyl isocyanate | 4-Br | O |

EXAMPLE 8

The general procedure of Example 2 is repeated with the following isocyanates or isothiocyanates instead of the 4-trifluoromethyl)phenyl isocyanate used therein to provide the corresponding carbamoyl products.

| Isocyanate | XIII (R¹ = CH₃; Y = O) | |
|---|---|---|
| | R2 | X |
| p-tolyl isocyanate | 4-CH₃ | O |
| o-tolyl isothiocyanate | 2-CH₃ | S |
| 3-chlorophenyl isothiocyanate | 3-Cl | S |
| 4-methoxyphenyl isocyanate | 4-OCH₃ | O |
| 2-ethylphenyl isocyanate | 2-CH₂CH₃ | O |
| 2-chlorophenyl isocyanate | 2-Cl | O |
| 3-chlorophenyl isocyanate | 3-Cl | O |
| 4-chlorophenyl isocyanate | 4-Cl | O |
| 2-chlorophenyl isothiocyanate | 2-Cl | S |
| 4-chlorophenyl isothiocyanate | 4-Cl | S |
| 2-methoxyphenyl isocyanate | 2-OCH₃ | O |
| 3-methoxyphenyl isocyanate | 3-OCH₃ | O |
| 2-methoxyphenyl isothiocyanate | 2-OCH₃ | S |
| 4-methoxyphenyl isothiocyanate | 4-OCH₃ | S |
| 2-bromophenyl isothiocyanate | 2-Br | S |
| 4-bromophenyl isocyanate | 4-Br | O |

EXAMPLE 9

The general procedure of Example 3, Step B is repeated with the following isocyanates or isothiocyanates instead of the 4-trifluoromethyl)phenyl isocyanate used therein to provide the corresponding carmaboyl products.

| Isocyanate | XIII (R¹ = CH₃; Y = NH) | |
|---|---|---|
| | R2 | X |
| p-tolyl isocyanate | 4-CH₃ | O |
| o-tolyl isothiocyanate | 2-CH₃ | S |
| 3-chlorophenyl isothiocyanate | 3-Cl | S |
| 4-methoxyphenyl isocyanate | 4-OCH₃ | O |
| 2-ethylphenyl isocyanate | 2-CH₂CH₃ | O |
| 2-chlorophenyl isocyanate | 2-Cl | O |
| 3-chlorophenyl isocyanate | 3-Cl | O |
| 4-chlorophenyl isocyanate | 4-Cl | O |
| 2-chlorophenyl isothiocyanate | 2-Cl | S |
| 4-chlorophenyl isothiocyanate | 4-Cl | S |
| 2-methoxyphenyl isocyanate | 2-OCH₃ | O |
| 3-methoxyphenyl isocyanate | 3-OCH₃ | O |
| 2-methoxyphenyl isothiocyanate | 2-OCH₃ | S |
| 4-methoxyphenyl isothiocyanate | 4-OCH₃ | S |
| 2-bromophenyl isothiocyanate | 2-Br | S |
| 4-bromophenyl isocyanate | 4-Br | O |

EXAMPLE 10

The procedure described in Example 1, Step A is repeated with the exception that the methanethiol used therein is replaced by the alkylthiols listed below to yield the corresponding S-alkyl cyanothioacetates which in turn are used as reactants in Step B of Example 1 to provide compounds of formula XIII.

| Thiol | Thioester | XIII (R² = 4-CF₃; Y = S, X = O); R¹ = |
|---|---|---|
| CH₃CH₂SH | CH₃CH₂SC(O)CH₂CN | CH₃CH₂— |
| (CH₃)₂CHSH | (CH₃)₂CHSC(O)CH₂CN | (CH₃)₂CH— |
| CH₃(CH₂)₃SH | CH₃(CH₂)₃SC(O)CH₂CN | CH₃(CH₂)₃— |
| (CH₃)₂CHCH₂SH | (CH₃)₂CHCH₂SC(O)CH₂CN | (CH₃)₂CHCH₂— |
| CH₃(CH₂)₂SH | CH₃(CH₂)₂SC(O)CH₂CN | CH₃(CH₂)₂— |
| CH₃CH₂CH(CH₃)SH | CH₃CH₂CH(CH₃)SC(O)CH₂CN | CH₃CH₂CH(CH₃)— |
| CH₃(CH₂)₄SH | CH₃(CH₂)₄SC(O)CH₂CN | CH₃(CH₂)₄— |
| (CH₃)₂CH(CH₂)₂SH | (CH₃)₂CH(CH₂)₂SC(O)CH₂CN | (CH₃)₂CH(CH₂)₂— |
| CH₃CH₂CH(CH₃)CH₂SH | CH₃CH₂CH(CH₃)CH₂SC(O)CH₂CN | CH₃CH₂CH(CH₃)CH₂— |
| CH₃(CH₂)₅SH | CH₃(CH₂)₅SC(O)CH₂CN | CH₃(CH₂)₅— |

EXAMPLE 11

The procedure described in Example 1, Step A is repeated with the exception that the methane thiol used therein is replaced by the alcohols listed below to yield the corresponding cyanoacetates which in turn are used as starting materials in Example 2 to provide compounds of formula XIII.

| Alcohol | Ester | XIII (R² = 4-CF₃; Y = O, X = O) R¹ = |
|---|---|---|
| CH₃CH₂OH | CH₃CH₂OC(O)CH₂CN | CH₃CH₂— |
| (CH₃)₂CHOH | (CH₃)₂CHOC(O)CH₂CN | (CH₃)₂CH— |
| CH₃(CH₂)₃OH | CH₃(CH₂)₃OC(O)CH₂CN | CH₃(CH₂)₃— |
| (CH₃)₂CHCH₂OH | (CH₃)₂CHCH₂OC(O)CH₂CN | (CH₃)₂CHCH₂— |
| CH₃(CH₂)₂OH | CH₃(CH₂)₂OC(O)CH₂CN | CH₃(CH₂)₂— |
| CH₃CH₂CH(CH₃)OH | CH₃CH₂CH(CH₃)OC(O)CH₂CN | CH₃CH₂CH(CH₃)— |
| CH₃(CH₂)₄OH | CH₃(CH₂)₄OC(O)CH₂CN | CH₃(CH₂)₄— |
| (CH₃)₂CH(CH₂)₂OH | (CH₃)₂CH(CH₂)₂OC(O)CH₂CN | (CH₃)₂CH(CH₂)₂— |

| | | XIII ($R^2$ = 4-CF$_3$; |
|---|---|---|
| Alcohol | Ester | Y = O, X = O) |
| CH$_3$CH$_2$CH(CH$_3$)CH$_2$OH | CH$_3$CH$_2$CH(CH$_3$)CH$_2$OC(O)CH$_2$CN | CH$_3$CH$_2$CH(CH$_3$)CH$_2$— |
| CH$_3$(CH$_2$)$_5$OH | CH$_3$(CH$_2$)$_5$OC(O)CH$_2$CN | CH$_3$(CH$_2$)$_5$— |

EXAMPLE 12

The procedure described in Example 3, Step A is repeated with the exception that the methylamine used therein is replaced with the amines listed below to yield the corresponding cyanoacetamides which in turn are used as reactants in Step B of Example 3 to provide compounds of formula XIII.

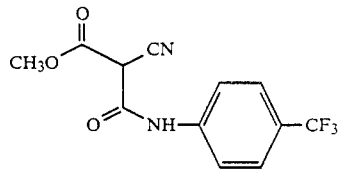

| Amine | Amide | XIII ($R^2$ = 4-CF$_3$; Y = NH, X = O) |
|---|---|---|
| CH$_3$CH$_2$NH$_2$ | CH$_3$CH$_2$NHC(O)CH$_2$CN | $R^1$ = CH$_3$CH$_2$— |
| (CH$_3$)$_2$CHNH$_2$ | (CH$_3$)$_2$CHNHC(O)CH$_2$CN | (CH$_3$)$_2$CH— |
| CH$_3$(CH$_2$)$_3$NH$_2$ | CH$_3$(CH$_2$)$_3$NHC(O)CH$_2$CN | CH$_3$(CH$_2$)$_3$— |
| (CH$_3$)$_2$CHCH$_2$NH$_2$ | (CH$_3$)$_2$CHCH$_2$NHC(O)CH$_2$CN | (CH$_3$)$_2$CHCH$_2$— |
| CH$_3$(CH$_2$)$_2$NH$_2$ | CH$_3$(CH$_2$)$_2$NHC(O)CH$_2$CN | CH$_3$(CH$_2$)$_2$— |
| CH$_3$CH$_2$CH(CH$_3$)NH$_2$ | CH$_3$CH$_2$CH(CH$_3$)NHC(O)CH$_2$CN | CH$_3$CH$_2$CH(CH$_3$)— |
| CH$_3$(CH$_2$)$_4$NH$_2$ | CH$_3$(CH$_2$)$_4$NHC(O)CH$_2$CN | CH$_3$(CH$_2$)$_4$— |
| (CH$_3$)$_2$CH(CH$_3$)CH$_2$NH$_2$ | (CH$_3$)$_2$CH(CH$_2$)$_2$NHC(O)CH$_2$CN | (CH$_3$)$_2$CH(CH$_2$)$_2$— |
| CH$_3$CH$_2$CH(CH$_3$)CH$_2$NH$_2$ | CH$_3$CH$_2$CH(CH$_3$)CH$_2$NHC(O)CH$_2$CN | CH$_3$CH$_2$CH(CH$_3$)CH$_2$— |
| CH$_3$(CH$_2$)$_5$NH$_2$ | CH$_3$(CH$_2$)$_5$NHC(O)CH$_2$CN | CH$_3$(CH$_2$)$_5$— |

What is claimed is:

1. A compound having the formula

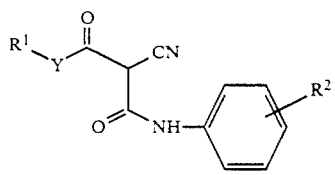

wherein
$R^1$ is C$_{1-10}$alkyl;
X is O or S;
Y is S, or NH; $R^2$ is halo-substituted C$_{1-5}$alkyl;
or a pharmaceutically acceptable salt thereof.

2. A compound of claim 1 wherein X is O.

3. A compound of claim 1 wherein $R^2$ is trifluoromethyl.

4. A compound of claim 1 wherein Y is O.

5. The compound of claim 1 which is

6. A compound of claim 1 wherein Y is NH.

7. The compound of claim 1 which is

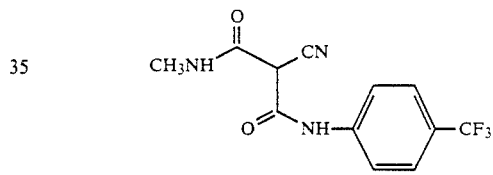

8. A compound of claim 1 wherein Y is S.

9. The compound of claim 1 which is

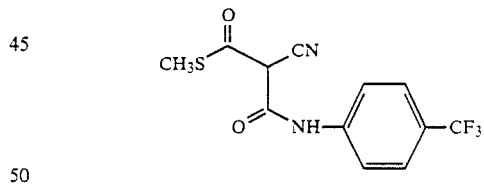

10. A method for treating a mammalian host suffering from arthritic condition which comprises administering to said host an anti-arthritic effective dose of a compound of claim 1.

11. A method for treating a mammalian host suffering from an inflammatory condition which comprises administering to said host an anti-inflammatory effective dose of a compound of claim 1.

12. A pharmaceutical composition which comprises an anti-arthritic effective amount of a compound of claim 1 and a pharmaceutically acceptable carrier.

13. A pharmaceutical composition which comprises an anti-inflammatory effective amount of a compound of claim 1 and a pharmaceutically acceptable carrier.

* * * * *